US007112215B2

(12) United States Patent
Xiao et al.

(10) Patent No.: US 7,112,215 B2

(45) Date of Patent: Sep. 26, 2006

(54) DIGITIZED CONTROL THREE-DIMENSIONAL SPINAL ORTHOPAEDIC DEVICE

(75) Inventors: Shiyou Xiao, Beijing (CN); Zaijie Guan, Beijing (CN)

(73) Assignee: Shiyou Xiao, Beijing (CN)

( * ) Notice: Subject to any disclaimer, the term of this patent is extended or adjusted under 35 U.S.C. 154(b) by 505 days.

(21) Appl. No.: 10/311,168

(22) PCT Filed: Apr. 29, 2001

(86) PCT No.: PCT/CN01/00678
§ 371 (c)(1),
(2), (4) Date: Nov. 30, 2002

(87) PCT Pub. No.: WO01/95839

PCT Pub. Date: Dec. 20, 2001

(65) Prior Publication Data

US 2003/0139777 A1 Jul. 24, 2003

(30) Foreign Application Priority Data

Jun. 5, 2000 (CN) .................................. 00235851

(51) Int. Cl.
*A61H 1/02* (2006.01)
*A61F 5/00* (2006.01)

(52) U.S. Cl. ...................... 606/242; 606/243; 606/245; 601/26

(58) Field of Classification Search .................... 601/5, 601/23, 24, 26, 33, 34, 35; 128/845; 602/32, 602/33, 36, 38; 606/240, 242, 243, 244; 5/608, 609

See application file for complete search history.

(56) References Cited

U.S. PATENT DOCUMENTS 2,179,595 A * 11/1939 McManis .................... 606/245

(Continued)

FOREIGN PATENT DOCUMENTS

CN 1032737 A 5/1989

(Continued)

*Primary Examiner*—Danton DeMille
(74) *Attorney, Agent, or Firm*—Tong Li

(57) ABSTRACT

This present invention relates to a digitized control three-dimensional spinal orthopaedic device for cure injured spinal. The device comprises a bed body, a head-chest plate and a breech-leg plate. The bed body has a frame configuration, and comprises a top bed body and a bottom bed body. The head-chest plate is fixed on the top bed body. A traction means of the head-chest plate and an angle means of the breech-leg plate are fixed into the top bed body. The breech-leg plate is supported by a swinging arm. A left-to-right angle means is located under the breech-leg plate. A connecting shaft of the angle means is connected to the up-to-down swinging arm by a cross rod, so the head-chest plate is integrated with the breech-leg plate. The present spinal orghopaedic device can enable the bed body to go up and down automatically, the head-chest plate can vibrate and be drawn at a high or low speed, and the breech-leg plate moves up to down, rotates left to right and vibrate. The device can correct the three-dimensional pathologic change of the spine by use of the digitized control, and can employ quantified treatment accurately in order to ensure security and relibility.

6 Claims, 3 Drawing Sheets

U.S. PATENT DOCUMENTS

| | | | | | |
|---|---|---|---|---|---|
| 3,771,518 | A | * | 11/1973 | Greissing | 606/243 |
| 4,579,109 | A | * | 4/1986 | Lundblad | 606/243 |
| 4,649,905 | A | * | 3/1987 | Barnes | 606/245 |
| 4,850,343 | A | | 7/1989 | Scott | |
| 5,860,899 | A | * | 1/1999 | Rassman | 482/142 |
| 5,926,002 | A | * | 7/1999 | Cavanaugh et al. | 318/672 |
| 6,277,141 | B1 | * | 8/2001 | Lake | 606/243 |

FOREIGN PATENT DOCUMENTS

| | | | |
|---|---|---|---|
| CN | 2170743 | Y | 7/1994 |
| CN | 1090998 | A | 8/1994 |
| CN | 1149443 | A | 5/1997 |
| CN | 2323754 | Y | 6/1999 |
| WO | 87/03799 | | 7/1987 |

* cited by examiner

DIGITIZED CONTROL THREE-DIMENSIONAL SPINAL ORTHOPAEDIC DEVICE

This application is a §371 application of PCT/CN01/00678, filed on 29 Apr. 2001, which in turn claims priority to CN application 00235851.4 filed 5 Jun. 2000. Each of the above identified applications is incorporated by reference herein.

FIELD OF THE INVENTION

This practical new product is a numerically-controlled 3D vertebra rectifier. It is a therapeutic apparatus used to cure lumbar vertebra disc protrusion, cervical spondylosis, and vertebra soft tissue injury disease of breast/waist rear-joint dysfunction.

BACKGROUND OF THE INVENTION

Lumbar vertebra disc protrusion, cervical spondylosis, and vertebra soft tissue injury disease of breast/waist rear-joint dysfunction are commonly-seen and frequently-occurring diseases. They bring great pains to patients and the main cause of their pathologic changes is that there are some three-dimensional changes between the patient's sick centrums. The commonly-used 3D vertebra traction bed is used to rectify the changes of sick centrums at the three-dimensional direction, making it return to normal. The vertebra 3D bed for quick traction is implemented by using hydraulic driving unit. Because the hydraulic action of the hydraulic driving unit is slow and cannot precisely and quantitatively cure the patient, it is difficult for it to ensure the safety and reliability of treatment.

SUMMARY OF THE INVENTION

This new practical product is intended to provide a numerically-controlled vertebra rectifier. It can implement such functions as automatic rising and lowering of bed body and such actions as up-tilting, down-tilting, left/right rotating and dithering of hip/leg plates. It can be used to correct the three-dimensional changes of sick centrums and implement three-axle two-link numeric control. It can precisely and quantitatively cure the patient and can ensure the safety and reliability of the treatment.

The goal of this new practical product is implemented through a numerically-controlled 3D vertebra rectifier including bed body, head/breast plate, and hip/leg plates. it has the following features: the said bed body is of the frame structure and divided into upper and lower bed bodies, in which there is equipped with an automatic rising/lowering mechanism; the said head/breast plate is installed on the upper bed body; in the upper bed body is mounted with the traction mechanism of head/breast plate and the angled mechanism of hip/leg plate; the hip/leg plate is supported with rotary supporting arm. The lower part of the hip/leg plate has the left-/right-rotating mechanism. The connecting bar of the angled mechanism is connected to the up-/down-tilting rotating arm of the hip/leg plate through a transverse axle so that the head/breast plate and the hip/leg plate form an integral unit.

DETAILED DESCRIPTION OF THE INVENTION

Figure 1:
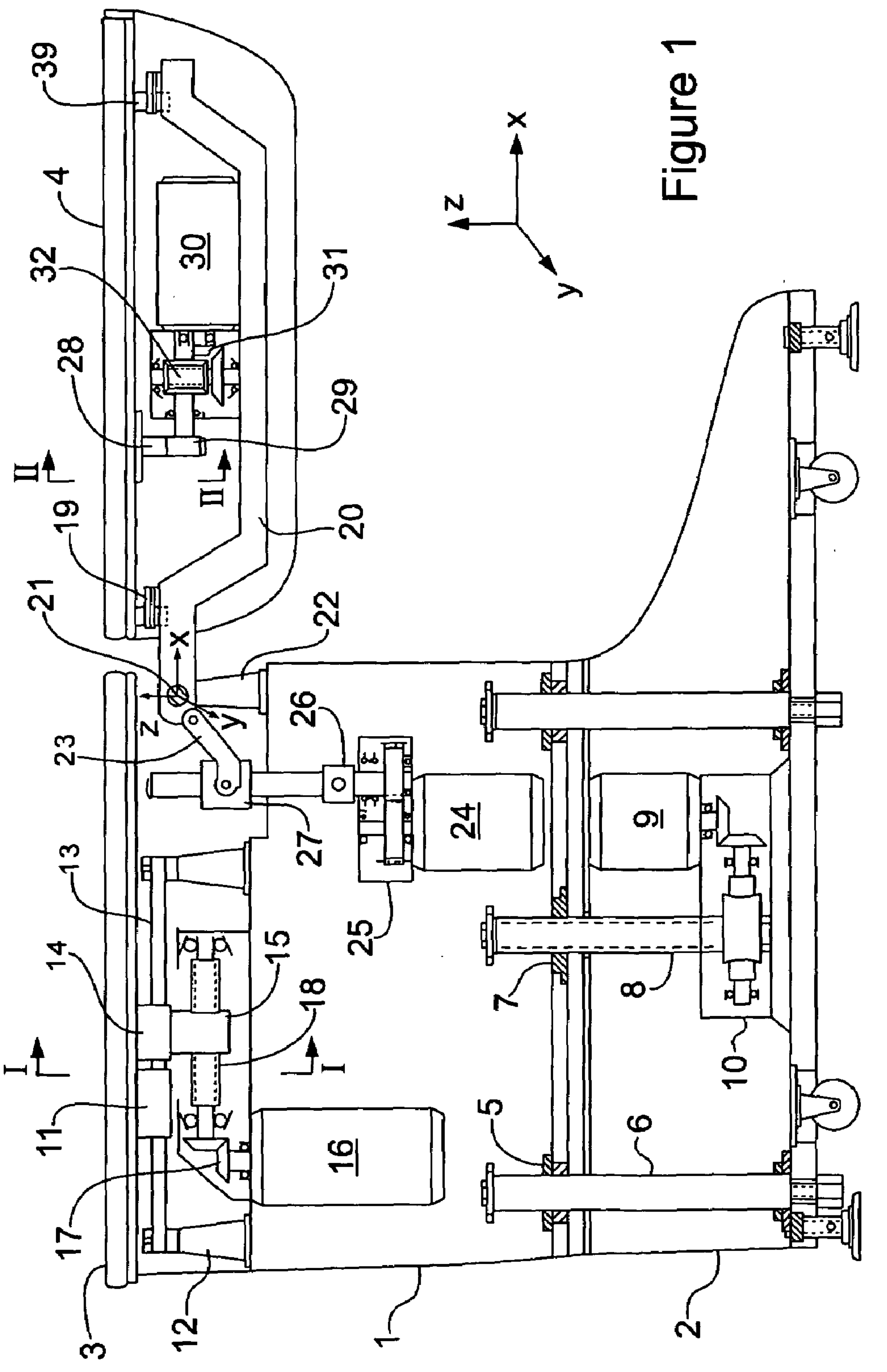
FIG. 1 is the schematic diagram of the structure of this new practical product.
Figure 3:
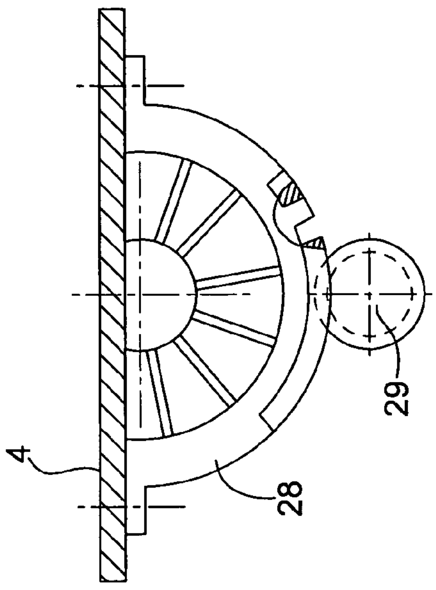
FIG. 3 is the II—II sectional view of FIG. 1.
Figure 2:
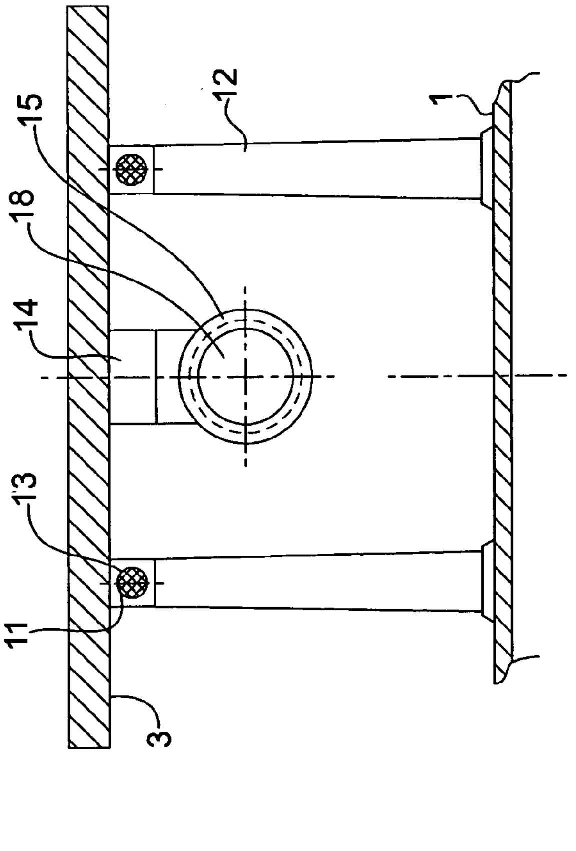
FIG. 2 is the I—I sectional view of FIG. 1.
Figure 4:
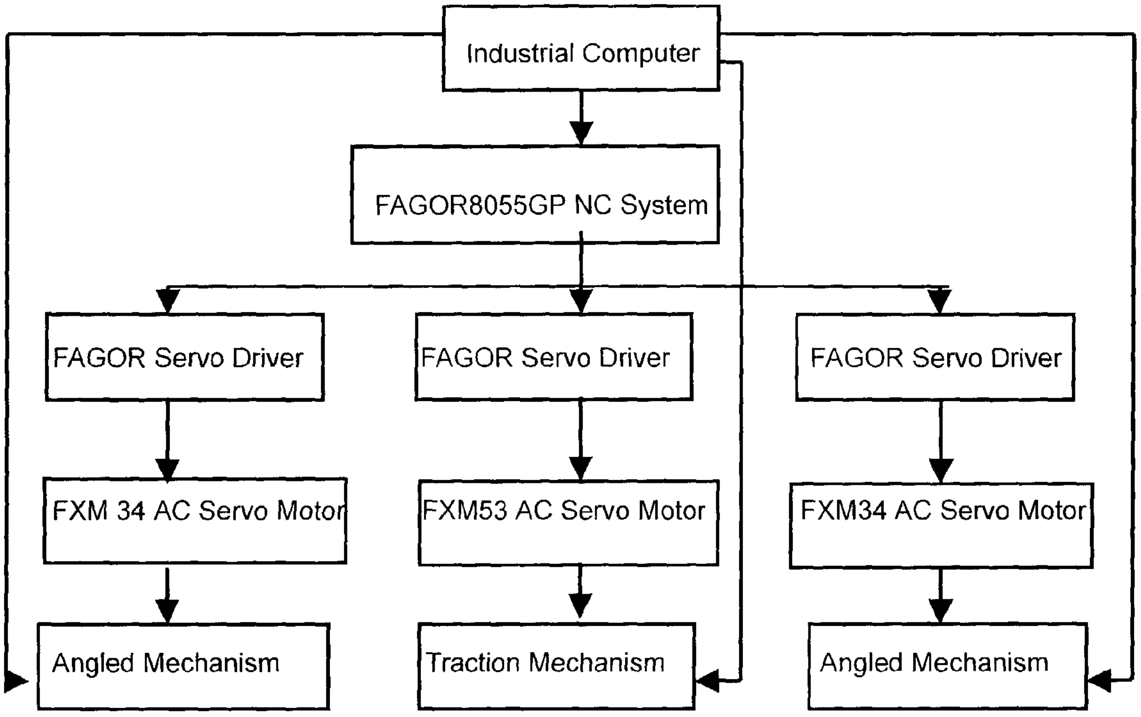
FIG. 4 is the schematic diagram of numerical control.

This new practical product is a numerically-controlled vertebra rectifier and it includes the bed body, head/breast plate (3), and hip/leg plate (4). The bed body is of a frame structure and it is divided into the upper bed boy (1) and the lower bed body (2). Inside the bed body, there is equipped with an automatic rising/lowering mechanism. The head/breast plate (3) is on the upper bed body (1). Inside the upper bed body (1), there is installed with the traction mechanism of the head/breast plate (3) and the angled mechanism of the hip/leg plate (4).

The hip/leg plate (4) is supported by the rotary supporting arm (20). In the lower part of the hip/leg plate (4), there is equipped with the left-/right-rotating mechanism. The connecting bar (23) of the angled mechanism is connected to the up-/down-tilting supporting arm (20) of the hip/leg plate (4) through transverse axle (21), which makes the head/breast (3) and the hip/leg plate (4) being an integrity.

The automatic rising/lowering mechanism installed inside the bed body is composed of guide sleeve (5), guide pole (7), threaded sleeve (7), trapezoidal rising/lowering lead screw (8), motor (9) and accessory worm gear case (10). Among these parts, the guide sleeve (5) fixed at the four corners of upper base plate of upper bed body (1) is connected to the four guide poles (6) fixed at the four corners of lower base plate of the lower bed body (2), and the threaded sleeve (7) fixed in the middle of the lower base plate of the upper bed body (1) is connected to the trapezoidal rising/lowering lead screw (8) fixed on the lower base plate of the lower bed body (2). On the base plate of the upper bed body (1), there is installed with motor (9), accessory worm gear box (10) and trapezoidal rising/lowering lead screw (8). When the upper bed body (1) needs to rise/lower along Axis Z upon the requirements of therapy, it can control the rotation of motor (9) with the aid of the set computer program and then drive the trapezoidal lead screw (8) to rotate via the accessory worm gear box (10). Thus, while it makes the threaded sleeve (7) of the upper bed body (1) rising or lowering along the trapezoidal lead screw (8), it can more upward or downward along the four guide poles (6). As a result, the automatic rising/lowering of the bed body (1) can be implemented within the range from 750 mm to 1200 mm.

The head/breast plate (3) can use the traction mechanism installed in the upper bed body (1) to implement the quick or slow traction or dithering along X-axis. The traction mechanism is composed of two guide sleeves (11), two longitudinal guide poles (131, connecting body (14), and lead screw nut (15), servodriving system. In this mechanism, the lower part of the head/breast plate (3) sliding-fits with two longitudinal guide poles (13) on the frame supporting seat (12) of the upper bed body (1) along the two guide sleeves (11) fixed on two sides of X-axis direction, the connecting unit (14) fixed in the middle part below head/breast plate (3) is connected to the lead screw nut (15), and the lead screw nut (15) fits with the ball screw (18) in the servodriving system. The servo-driving system is composed of servo motor (16) installed in the upper bed body (1), gear box (17) and ball screw suite (18). Then it works, upon the requirements of the patient, set up the treatment traction distance and input it into the computer and the computer can control the rotation of the driving servo motor (16) following the set program and through FAGOR8055GP numerically-controlled system and servo driving system and drive the ball screw suite (18) via gear box (17) to rotate, so as to make the connecting unit (14) to more forward and backward and implement the quick or slow reciprocating motion of the head/breast plate (3) within the range from 0 to 70 mm. Its traction force can be up to 4800N. If in the program the short-distance and high-frequency reciprocating motion is set, the dithering function is activated. The actual data of quick and slow traction and dithering of the head/breast plate is feedback by the coder in the servo motor (16) to the computer for computation and correction, so as to complete the closed circuit control cycle. At the same time, this procedure will be displayed and recorded in the computer.

The hip/leg plate (4) can sway around the uptilting/downtilting angles of Axis Y with the aid of the angled mechanism installed in the upper bed body. This angled mechanism is composed of servo motor (24) installed in the upper bed body, gear box (25), universal coupling (26), rotating lead screw suite (27) and connecting bar (23). Along the X-axis direction of the plan under the hip/leg plate (4), there are two arm supports (39), which enable it to connect to the supporting arm (20) that can sway at the up-tilting/downtilting angles. The left part of supporting arm (20) is connected to transverse axle (21) on the frame support (22) of the upper bed body (1). The left end of the supporting arm (20) is connected to the connecting bar (23) of the angled mechanism. When it is used, upon the requirements of the patient the up-tilting or down-tilting angle that the hip/leg plate needs for treatment should be set up and input into the computer. The computer shall control the rotation of the driving servo motor (24) according to the settings in the program and through the FAGOR8055GP numerically-controlled system and the servo driving system, then with the aid of the gear box (25), it will drive the lead screw suite (27) to drive the connecting bar (23) to rotate, so as to make the supporting arm (20) sway along Y axis of supporting arm transverse axle (21) at an up-tilting angle of 15 or a downtilting angle of 25 and then locate. The actual angle will be feedback to the computer via the coder in the servo motor (24) for computation and correction, so as to finish the closed control cycle. In this process, such data will be displayed on and recorded in the computer.

The hip/leg plate (4) can rotate left and right around X axis and dither. This is implemented by the left and right rotating mechanism set up under the hip/leg plate (4). The rotating mechanism is composed of the rotating servo motor (30) installed under the supporting arm (2), gear box (31), rotating worm gear suite (32), small gear (29) and semi-circle big gear (28) engaging with the small gear (29). The semi-circle big gear (28) is fixed on the axle wire under the plan of the hip/leg plate. When it is in operation, the left/right rotating angle should be set up for the hip/leg plate upon the requirements of the patient and then input into the computer. The computer will, according to the set program and through the FAGOR8055GP numerically-controlled system and the servo driving system, control the rotation of the driving servo motor (30), then the gear box (31) will help to drive the rotating worm gear suite (32) and then the small gear (29), so as to make the big gear (28) to drive the hip/leg plate to quickly rotate at any angle between left and right 25 degrees along the X axis of the axle line. The torque here can be up to 1500N. if a small angle and quick rotation is set in the set program, the hip/leg plate will dither around X axis. The left/right rotation of the hip/leg plate (4) and the traction action of the head/breast plate (3) can synchronize for linkage. Its actual rotary angle can be feedback to the computer via the coder in the servo motor (30) for computation and modification, so as to finish the closed control cycle. This process will be displayed and recorded in the computer.

EXAMPLE

This new practical 3D numerically-controlled vertebra rectifier can implement the following actions: automatic rising/lowering of bed body along Z axis, quick or slow traction and dithering of the head/breast plate along X axis, swaying of the hip/leg plate along Y axis at an up-tilting/down-tilting angle, and left/right rotation and dithering of the hip/leg plate along X axis, so as to correct the three-dimensional change between sick centrums. The vertebra rectifier uses the industrially-controlled computer and FAGOR8055GP numerically-controlled system as the controllers and uses the three-axle and two-linkage FAGOR digitalized servo driving system as the actuator to implement the three-dimensional action via the servo motor, so it can strictly control various action quantity, precisely quantitative treatment and ensure the safety and reliability of the treatment.

Its treatment features are as follows:

1. Quick distance traction, which will not produce time effect that may hurt the body of a patient so that the patient will feel no pain.
2. Rotation at a fixed direction and fixed angle. Its shear force and torque force not only can correct the rotary shift between sick centrums but also can relax the connection of local tissues.
3. Continuous and alternate dual-way conjugated rotation, which obviously improve the one-off treatment success rate.
4. It can locate the correct centrums for treatment so as to concentrate the force where the sick centrums are and therefore improve the treatment effect.
5. All motion parameters of this equipment have passed the strict biomechanics experiment on human body, which has proved that they are safe and reliable. It not only meets the physiological requirement of human body but also inherits and leverages the advantages of traditional Chinese massage techniques and represents the modern therapy techniques of cervical and lumbar vertebra spondylosis.

What is claimed is:

1. A numerically-controlled (NC) 3D vertebra rectifier comprising a bed body, a head and breast plate, and a hip and leg plate; wherein, said bed body is of a frame structure and is divided into an upper bed body and a lower bed body; said bed body is installed with an automatic rising and lowering mechanism; said head and breast plate and said hip and leg plate are arranged along a longitudinal axis; said head and breast plate is installed on said upper bed body; a traction mechanism of said head and breast plate and an angled mechanism of said hip and leg plate is installed in said upper bed body; said hip and leg plate is supported by a rotary supporting arm which is positioned along the longitudinal axis; the lower part of said hip and leg plate is set up with a rotation mechanism about the longitudinal axis; and a connecting bar on said angled mechanism is connected to said rotary supporting arm of said hip and leg plate via a transverse axle, which makes said head and breast plate and said hip and leg plate as an integrity, wherein, said automatic rising and lowering mechanism installed in said bed body comprises four guide sleeves, four guide poles, a threaded sleeve, a trapezoidal rising and lowering lead screw, a motor, and a worm gear box suite; said four guide sleeves fixed at the four corners of an upper base plate under said upper bed body is connected to said four guide poles fixed at the four corners of a lower base plate under said lower bed body; said thread sleeve fixed in the middle of said upper base plate of said upper bed body is connected to said trapezoidal rising and lowering lead screw fixed on said lower base plate of said lower bed body; said motor, said worm gear box suite, and said trapezoidal rising and lowering lead screw are installed on said lower base plate of said lower bed body and said motor drives said trapezoidal rising and lowering lead screw via said worm gear box suite.

2. A numerically-controlled (NC) 3D vertebra rectifier comprising a bed body, a head and breast plate, and a hip and leg plate; wherein, said bed body is of a frame structure and is divided into an upper bed body and a lower bed body; said bed body is installed with an automatic rising and lowering mechanism; said head and breast plate and said hip and lea plate are arranged along a longitudinal axis; said head and breast plate is installed an said upper bed body; a traction mechanism of said head and breast plate and an angled mechanism of said hip and leg plate is installed in said upper bed body; said hip and leg plate is supported by a rotary supporting arm which is positioned along the longitudinal axis; the lower part of said hip and leg plate is set up with a rotation mechanism about the longitudinal axis; and a connecting bar on said angled mechanism is connected to said rotary supporting arm of said hip and leg plate via a transverse axle, which makes said head and breast plate and said hip and leg plate as an integrity, wherein, said traction mechanism of said head and breast plate comprises two guide sliding sleeves, two longitudinal guide poles, a connecting unit, a lead screw nut, and a servo driving system; said two guide sliding sleeves fixed on both sides along the longitudinal axis under said head and breast plate has a sliding fit with said two longitudinal guide poles on a frame support of said upper bed body; said connecting unit fixed in the middle part below said head and breast plate is connected to said lead screw nut; and said lead screw nut fits with a ball lead screw in said servo driving system.

3. The NC 3D vertebra rectifier according to claim 2, wherein, said servo driving system comprises a servo motor, gear box, and a ball lead screw suite installed in the upper bed body.

4. A numerically-controlled (NC) 3D vertebra rectifier comprising a bed body, a head and breast plate, and a hip and leg plate; wherein, said bed body is of a frame structure and is divided into an upper bed body and a lower bed body; said bed body is installed with an automatic rising and lowering mechanism; said head and breast plate and said hip and leg plate are arranged along longitudinal axis; said head and breast plate is installed on said upper bed body: a traction mechanism of said head and breast plate and an angled mechanism of said hip and leg plate is installed in said upper bed body; said hip and leg plate is supported by a rotary supporting arm which is positioned along the longitudinal axis; the lower part of said hip and leg plate is set up with a rotation mechanism about the longitudinal axis; and a connecting bar on said angled mechanism is connected to said rotary supporting arm of said hip and leg plate via a transverse axle, which makes said head and breast plate and said hip and leg plate as an integrity, wherein, two arm supports are set up along the longitudinal axis on each end of a lower surface of said hip and leg plate, said two arm supports are connected to said rotary supporting arm, which can sway at an up-tilting and down-tilting angle along the longitudinal axis, via two axle pins; the part of said rotary supporting arm which is closer to said head and breast plate is connected to said transverse axle on a frame support of said upper bed body; and the end of said rotary supporting arm which is closer to said head and breast plate is connected to said connecting bar of said angled mechanism.

5. The NC 3D vertebra rectifier according to claim 4, wherein, said angled mechanism comprises a servo motor, a gear box, an universal coupling, a swaying lead screw suite, and a connecting bar, which are installed in said upper bed body.

6. A numerically-controlled (NC) 3D vertebra rectifier comprising a bed body, a head and breast plate, and a hip and leg plate; wherein, said bed body is of a frame structure and is divided into an upper bed body and a lower bed body; said bed body is installed with an automatic rising and lowering mechanism; said head and breast plate and said hip and leg plate are arranged along a longitudinal axis; said head and breast plate is installed on said upper bed body; a traction mechanism of said head and breast plate and an angled mechanism of said hip and leg plate is installed in said upper bed body; said hip and leg plate is supported by a rotary supporting arm which is positioned along the longitudinal axis; the lower part of said hip and leg plate is set up with a rotation mechanism about the longitudinal axis; and a connecting bar on said angled mechanism is connected to said rotary supporting arm of said hip and leg plate via a transverse axle, which makes said head and breast plate and said hip and leg plate as an integrity, wherein, said left and right rotation mechanism set up under the said hip and leg plate comprises an angled servo motor installed on said rotary supporting arm, a gear box, an angled warm gear suite, a small gear, and a semi-circle big gear joggled with said small gear; and said semi-circle big gear is fixed on an axle wire below the plan of said hip and leg plate.

* * * * *